US012773345B2

(12) United States Patent
Hall et al.

(10) Patent No.: US 12,773,345 B2
(45) Date of Patent: Oct. 27, 2026

(54) THERMAL TRANSFER APPARATUS AND A METHOD OF USE THEREOF

(71) Applicant: Modular Thermal Technologies, LLC, Pompano Beach, FL (US)

(72) Inventors: Colin M. Hall, Pompano Beach, FL (US); Bradley J. Waugh, Pompano Beach, FL (US)

(73) Assignee: MODULAR THERMAL TECHNOLOGIES, LLC, Pompano Beach, FL (US)

( * ) Notice: Subject to any disclaimer, the term of this patent is extended or adjusted under 35 U.S.C. 154(b) by 493 days.

(21) Appl. No.: 18/488,477

(22) Filed: Oct. 17, 2023

(65) Prior Publication Data

US 2024/0122749 A1 Apr. 18, 2024

Related U.S. Application Data

(63) Continuation of application No. 29/878,766, filed on Jun. 27, 2023.

(60) Provisional application No. 63/379,969, filed on Oct. 18, 2022.

(51) Int. Cl.
*A61F 7/10* (2006.01)

(52) U.S. Cl.
CPC .......... *A61F 7/10* (2013.01); *A61F 2007/108* (2013.01)

(58) Field of Classification Search
CPC .................. A61F 2007/108; A61F 7/10; A61F 2007/0268; A61F 7/02; A61F 2007/0214; A61F 2007/0219; A61F 2007/0271; A61F 2007/0292; F25D 2303/08222; F25D 3/08
See application file for complete search history.

(56) References Cited

U.S. PATENT DOCUMENTS

| | | | |
|---|---|---|---|
| 2,152,019 | A | 3/1939 | Bates |
| 4,344,303 | A | 8/1982 | Kelly, Jr. |
| 4,964,402 | A | 10/1990 | Grim et al. |
| D343,686 | S | 1/1994 | Irwin, Jr. et al. |

(Continued)

OTHER PUBLICATIONS

Zou et al., Sustainable and Reusable Gelatin-Based Hydrogel "Jelly Ice Cubes" as Food Coolant. I: Feasibilities and Challenges, ACS Sustainable Chem. Eng. Jul. 20, 2021, 9, 46, pp. 15357-15364.

(Continued)

*Primary Examiner* — Tigist S Demie
(74) *Attorney, Agent, or Firm* — K&L Gates LLP

(57) ABSTRACT

A thermal transfer apparatus and a method of use thereof are provided. The thermal transfer apparatus comprises a first container comprising a first wall, and a second wall connected to the first wall at ends of each wall, thereby defining a first enclosed cavity. At least four protrusions extend from the first wall into the first enclosed cavity towards the second wall and each protrusion comprising a third wall defining a second enclosed cavity. At least four protrusions comprise at least two short protrusions and at least two long protrusions. The short protrusions extend a first distance from the first wall into the first enclosed cavity towards the second wall, and are positioned intermediate two or more of the long protrusions. The long protrusions extend a second distance from the first wall into the first enclosed cavity towards the second wall. The second distance is greater than the first distance.

19 Claims, 21 Drawing Sheets

(56) References Cited

U.S. PATENT DOCUMENTS

| | | | | |
|---|---|---|---|---|
| 5,505,720 | A | 4/1996 | Walters et al. | |
| 5,603,729 | A | 2/1997 | Brown et al. | |
| D403,778 | S | 1/1999 | Davis et al. | |
| 5,887,437 | A | 3/1999 | Maxim | |
| D408,923 | S | 4/1999 | Davis et al. | |
| D417,283 | S | 11/1999 | Davis et al. | |
| D442,285 | S | 5/2001 | Perry | |
| 6,904,956 | B2 | 6/2005 | Noel | |
| 7,055,575 | B2 | 6/2006 | Noel | |
| 7,240,720 | B2 | 7/2007 | Noel | |
| 7,980,242 | B1 | 7/2011 | Wilhelm | |
| 8,277,497 | B2 | 10/2012 | Noel | |
| D851,776 | S | 6/2019 | Weinstein | |
| D857,217 | S | 8/2019 | Fan et al. | |
| D1,040,359 | S | 8/2024 | Igaue et al. | |
| 2005/0145372 | A1 | 7/2005 | Noel | |
| 2008/0047684 | A1 | 2/2008 | Noel | |
| 2008/0233368 | A1 | 9/2008 | Hartmann et al. | |
| 2008/0275534 | A1 | 11/2008 | Noel | |
| 2009/0076574 | A1* | 3/2009 | Noel | B32B 3/28 607/109 |
| 2009/0076575 | A1 | 3/2009 | Noel | |
| 2013/0116760 | A1* | 5/2013 | Carson | A61F 7/10 607/104 |
| 2015/0238754 | A1 | 8/2015 | Loudin et al. | |
| 2015/0272775 | A1* | 10/2015 | Chehab | A61F 7/10 607/114 |
| 2017/0027744 | A1 | 2/2017 | Floyd | |
| 2022/0133529 | A1* | 5/2022 | Fleming | A61F 7/10 607/114 |
| 2023/0270103 | A1 | 8/2023 | Sevenler et al. | |
| 2024/0268995 | A1 | 8/2024 | Hall et al. | |
| 2025/0011019 | A1 | 1/2025 | Hall et al. | |

OTHER PUBLICATIONS

Zou et al., Sustainable and Reusable Gelatin-Based Hydrogel "Jelly Ice Cubes" as Food Coolant. II: Ideal Freeze—Thaw Conditions, ACS Sustainable Chem. Eng. Nov. 8, 2021, 9, 46, pp. 15365-15374.

Thermal MAX Heat Packs, posted Jul. 28, 2016 [online], [retrieved Mar. 19, 2025]. Retrieved from internet, https://www.youtube.com/watch?v=aOmq1 ShjaqE (Year: 2025).

Koonie Ice Packs for Injuries, posted Jul. 26, 2024 [online], [retrieved Mar. 11, 2025]. Retrieved from internet, https://www.amazon.com/ dp/B0DB7NVLMX?th=1 (Year: 2025).

CryoMAX®—Longest-Lasting Cooling Technology, retrieved May 19, 2025 from https://cryomax.com/?srsltid=AfmBOoqGmm84WP0r-QVVy25ri4njVx9gkIZ8cT3uV87GjzEKGyW24PVu, 6 pages.

Thermalmax, retrieved May 19, 2025 from https://thermalmax.com, 5 pages.

CryoMAX Cold Pack, found online Jun. 4, 2025 at https://www.amazon.com/dp/B001QFZL 1G?th=1 Reference dated Oct. 2, 2002.

Active Wrap Long Duration Ice Packs, posted Sep. 18, 2021 [online], [retrieved Mar. 11, 2025]. Retrieved from internet, https://activewrap.com/products/long-duration-post-op-ice-packs (Year: 2025).

Cryo-Max Cold Pack, posted Jan. 23, 2009 [online], [retrieved Mar. 11, 2025]. Retrieved from internet, https://www.amazon.com/dp/B001 QFZL 16?th=1 (Year: 2025).

* cited by examiner

THERMAL TRANSFER APPARATUS AND A METHOD OF USE THEREOF

RELATED APPLICATIONS

The present application is a continuation of U.S. Design patent application Ser. No. 29/878,766, filed Jun. 27, 2023, and claims priority to U.S. provisional patent application Ser. No. 63/379,969, filed Oct. 18, 2022, which is incorporated herein by reference in its entirety.

FIELD OF USE

The present disclosure relates to a thermal transfer apparatus and a method of use thereof.

BACKGROUND

Ice packs can be used to temporary alleviate swelling and/or pain from a portion of a body of a patient. Each different portion of the body may have a different size and shape and the same portion of the body may vary from patient to patient. There are challenges with designing an ice pack suitable for various portions of the body and for various patients.

SUMMARY

One aspect according to the present disclosure is directed to a thermal transfer apparatus comprising a first container comprising a first wall, and a second wall connected to the first wall at ends of each wall, thereby defining a first enclosed cavity. At least four protrusions extend from the first wall into the first enclosed cavity towards the second wall and each protrusion comprising a third wall defining a second enclosed cavity. At least four protrusions comprise at least two short protrusions and at least two long protrusions. The short protrusions extend a first distance from the first wall into the first enclosed cavity towards the second wall, and are positioned intermediate two or more of the long protrusions. The long protrusions extend a second distance from the first wall into the first enclosed cavity towards the second wall. The second distance is greater than the first distance. A first thermal transfer media is positioned within the first enclosed cavity. A second thermal transfer media is positioned within each second enclosed cavity. The first thermal transfer media has a first freezing point lower than a second freezing point of the second thermal transfer media.

It will be understood that the inventions disclosed and described in this specification are not limited to the aspects summarized in this Summary. The reader will appreciate the foregoing details, as well as others, upon considering the following detailed description of various non-limiting and non-exhaustive aspects according to this specification.

BRIEF DESCRIPTION OF THE DRAWINGS

The features and advantages of the examples presented herein, and the manner of attaining them, will become more apparent, and the examples will be better understood, by reference to the following description taken in conjunction with the accompanying drawings, wherein.

Corresponding reference characters indicate corresponding parts throughout the several views. The exemplifications set out herein illustrate certain embodiments, in one form, and such exemplifications are not to be construed as limiting the scope of the appended claims in any manner.

DESCRIPTION

Various examples are described and illustrated herein to provide an overall understanding of the structure, function, and use of the disclosed thermal supports and methods of using the thermal supports. The various examples described and illustrated herein are non-limiting and non-exhaustive. Thus, the invention is not limited by the description of the various non-limiting and non-exhaustive examples disclosed herein. Rather, the invention is defined solely by the claims. The features and characteristics illustrated and/or described in connection with various examples may be combined with the features and characteristics of other examples. Such modifications and variations are intended to be included within the scope of this specification. As such, the claims may be amended to recite any features or characteristics expressly or inherently described in, or otherwise expressly or inherently supported by, this specification. Further, Applicant reserves the right to amend the claims to affirmatively disclaim features or characteristics that may be present in the prior art. The various examples disclosed and described in this specification can comprise, consist of, or consist essentially of the features and characteristics as variously described herein.

Any references herein to “various examples”, “some examples”, “one example”, “an example”, “non-limiting examples”, or like phrases mean that a particular feature, structure, or characteristic described in connection with the example is included in at least one example. Thus, appearances of the phrases “in various examples”, “in some examples”, “in one example”, “in an example”, “in a non-limiting example”, or like phrases in the specification do not necessarily refer to the same example. Furthermore, the particular described features, structures, or characteristics may be combined in any suitable manner in an example or examples. Thus, the particular features, structures, or characteristics illustrated or described in connection with one example may be combined, in whole or in part, with the features, structures, or characteristics of another example or other examples without limitation. Such modifications and variations are intended to be included within the scope of the present examples.

Figure 1:
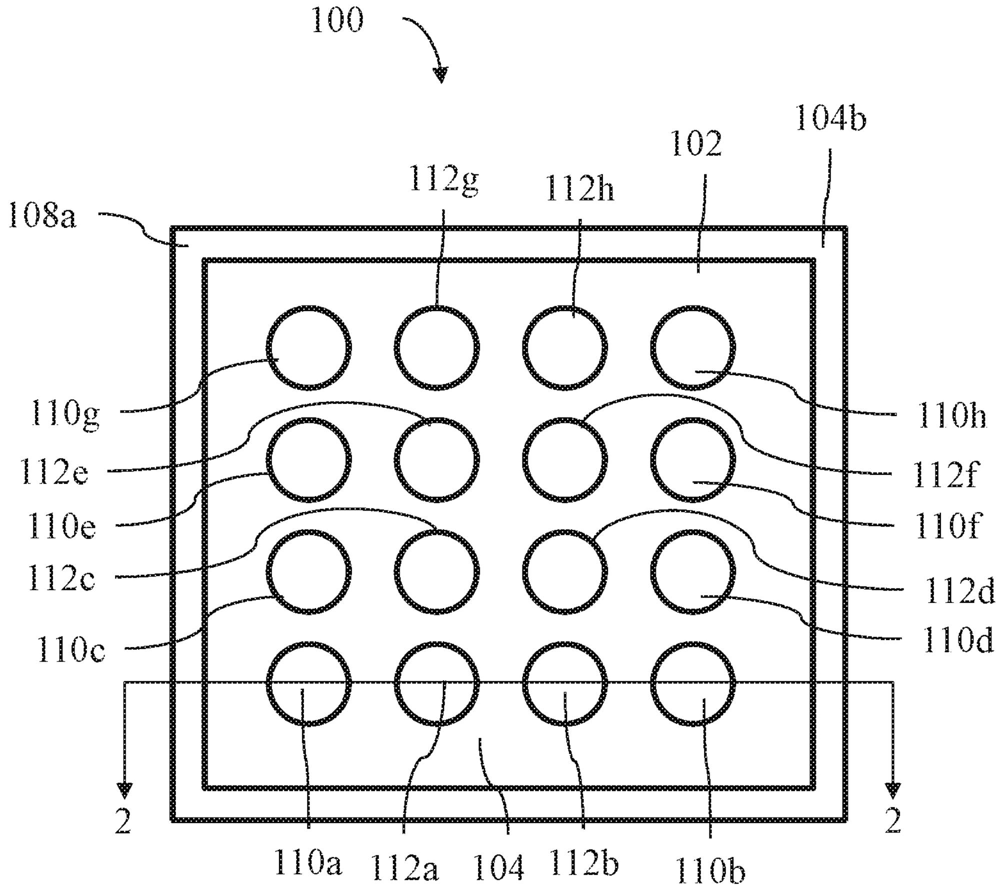
FIG. 1 is top view illustrating an example of a thermal transfer apparatus according to the present disclosure.
Figure 2:
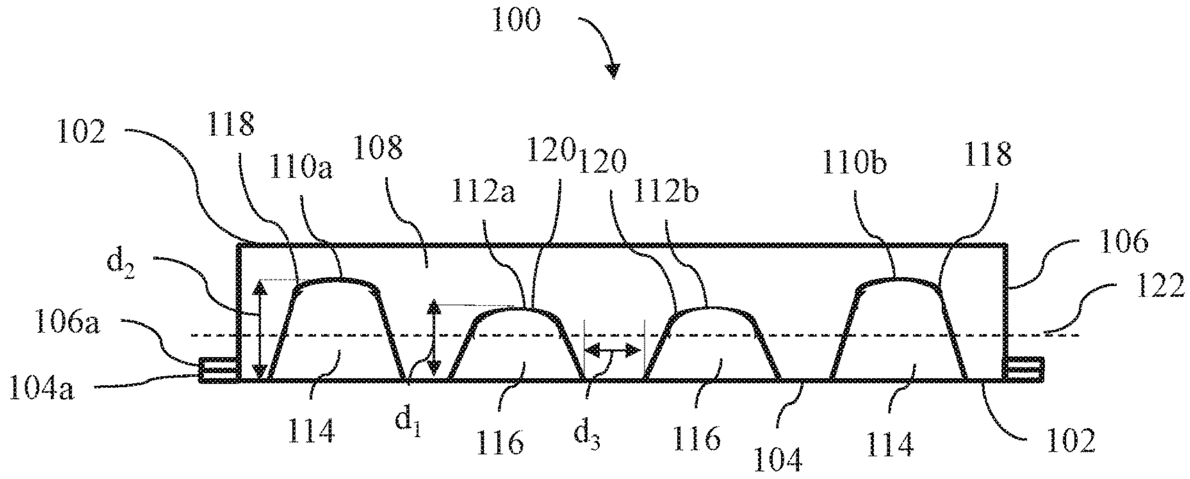
FIG. 2 is a cross-section view of the thermal transfer apparatus of FIG. 1.

Referring to FIGS. 1 and 2, a thermal transfer apparatus 100 is provided. The thermal transfer apparatus 100 comprises a first container 102 and at least four protrusions, such as, for example, 16 protrusions as shown in FIG. 1 or other amount of protrusions (not shown). The first container 102 comprises a first wall 104 and a second wall 106. The second wall 106 is connected to the first wall 104, thereby defining a first enclosed cavity 108. For example, the second wall 106 can comprise edges **106*a* and the first wall 104 can comprise edges 104*a*. The edges 104*a* and 106*a* can be fused together by, for example, heat sealing or other adhesive technique such that the first wall 104 is fused to the second wall 106. An example of the thermal transfer apparatus 100 is shown in FIGS. 6-16**.

Referring back to FIGS. 1 and 2, the at least four protrusions can comprise protrusions 110 and 112. The protrusions 110 and 112 extend from the first wall 104 into the first enclosed cavity 108 towards the second wall 106. For example, the protrusions 110 and 112 can be integral with the first wall 104.

As illustrated in FIG. 1, the protrusions 110 and 112 can comprise a rounded cross-section in a plane (e.g., plane 122 in FIG. 2, which is extending out of the page) parallel to the first wall 104. In various examples, the protrusions 110 and 112 can comprise a different shape. Referring to FIG. 2, each protrusion 110 and 112 can taper away from the first wall 104. For example, a diameter of the rounded cross-section of each protrusion 110 and 112 can decrease as one moves away from the first wall 104 towards the second wall 106.

The protrusions 110 and 112 comprise at least two long protrusions and at least two short protrusions, respectively. For example, protrusions 110 can be long protrusions and protrusions 112 can be short protrusions. The short protrusions 112 extend a first distance, $d_1$, from the first wall 104 into the first enclosed cavity 108 towards the second wall 106. The long protrusions 110 extend a second distance, $d_2$, from the first wall 104 into the first enclosed cavity 108 towards the second wall 106. The short protrusions 112 are positioned intermediate two or more of the long protrusions 110. In various examples, the long protrusions 110 extend along the perimeter of the thermal transfer apparatus 100 and the short protrusions 122 are in the interior of the thermal transfer apparatus 100 and can be surrounded by the long protrusions 110. The positioning of the long and short protrusions 110 and 112, respectively can enable the thermal transfer apparatus 100 to be more conformal to a portion of a body part it is brought into contact with.

The second distance, $d_2$, is greater than the first distance, $d_1$. For example, the second distance is greater than the first distance by at least 0.05 inches, such as, for example, by at least 0.1 inches, or by at least 0.125 inches. The first distance, $d_1$, can be in a range of 0.25 inch to 1.25 inch, such as, for example, 0.5 inch to 1 inch, 0.6 inch to 0.95 inches, or 0.7 inch to 0.9 inch. The second distance, $d_2$, can be in a range of 0.75 inches to 1.5 inches, such as, for example, 0.8 inch to 1.25 inches, 0.9 inch to 1.2 inches, or 0.95 inches to 1.2 inches.

In certain examples, the protrusions 110 and 112 can be arranged in a grid, such as, for example, four rows of four columns as illustrated in FIG. 1, five rows of five columns, or eight rows of eight columns, or other configuration. Each protrusion 110 and 112 can be spaced away from an adjacent protrusion a substantially uniform distance. For example, referring to FIG. 2, a third distance, $d_3$, between each protrusion 110 and 112 can be in a range of 0.1 inches to 1.25 inches, such as, for example, 0.3 inches to 1.25 inches, 0.5 inches to 1.1 inches, or 0.7 inches to 1.1 inches.

Each protrusion 110 and 112 comprises a third wall 118 and 120, respectively, defining a second enclosed cavities 114 and 116, respectively. In various examples, the third walls 118 and 120 are fused to the first wall 104 by, for example, heat sealing. The first wall 104, the second wall 106, and the third walls 118 and 120, each can comprise a thickness in a range of 0.5 mm to 5 mm such that the thermal transfer apparatus can remain pliable. In various examples, the first wall 104, the second wall 106, and the third walls 118 and 120 each can comprise plastic and may be substantially transparent.

A first thermal transfer media is positioned within the first enclosed cavity 108. A second thermal transfer media is positioned within each second enclosed cavity 114 and 116. The first thermal transfer media has a first freezing point lower than a second freezing point of the second thermal transfer media. For example, the first freezing point is lower than the second freezing point by at least 3 degrees Celsius, such as, for example, at least 5 degrees Celsius, or at least 8 degrees Celsius. The difference in freezing points enables the first thermal transfer media to be in a liquid state such that the thermal transfer apparatus is pliable while the second thermal transfer media can be in a solid state. Additionally, maintaining the first thermal transfer media in a liquid state can more efficiently maintain a temperature of the thermal transfer device while applied to a portion of a body of a patient.

The second freezing point can be no lower than temperatures found in conventionally available freezers so that the second thermal transfer media can be frozen in the conventionally available freezers. For example, the second freezing point can be in a range of −5 degrees Celsius to 5 degrees Celsius. The first freezing point can be lower than temperatures found in conventionally available freezer so that the first thermal transfer media may not freeze or the first freezing point may be configured to thaw efficiently at ambient temperature (e.g., 20 degrees Celsius+/−2 degrees Celsius). For example, the first freezing point can be in a range of −15 degrees Celsius to 0 degrees Celsius.

The first thermal transfer media and the second thermal transfer media, individually, can comprise water, glycol (e.g., propylene glycol), gelatin, a hydrogel, or a combination thereof. For example, the first thermal transfer media can comprise water and glycol and the second thermal transfer media can comprise water. In certain examples, the first thermal transfer media can comprise water, glycol, and gelatin and the second thermal transfer media can comprise water and gelatin. In various examples, the first thermal transfer media and/or second thermal transfer media can comprise gelatin based hydrogels, such as, for example, those as defined in "Sustainable and Reusable Gelatin-Based Hydrogel "Jelly Ice Cubes" as Food Coolant. I: Feasibilities and Challenges by Zou et al. ACS Sustainable Chem. Eng. 2021, 9, 15357-15364 and "Sustainable and Reusable Gelatin-Based Hydrogel "Jelly Ice Cubes" as Food Coolant. II: Ideal Freeze-Thaw Conditions by Zou et al. ACS Sustainable Chem. Eng. 2021, 9, 15365-15374, both hereby incorporated by reference.

In various examples, the first thermal transfer media and the second thermal transfer media, individually, further comprise chitosan. Chitosan can inhibit bacterial and/or fungal growth in the thermal transfer media. The bacterial and/or fungal growth may not be aesthetically desirable and/or unsanitary. The first thermal transfer media and/or second thermal transfer media can comprise a range of 0.01% by weight to 2% by weight Chitosan, such as, for example, 0.1% by weight to 2% by weight Chitosan, 0.1% by weight to 1% by weight Chitosan or 0.2% by weight to 0.9% by weight Chitosan.

The first thermal transfer media and/or second thermal transfer media can further comprise a dye. For example, the first thermal transfer media can be pink and the second thermal transfer media can be blue.

A method of removing heat with the thermal transfer apparatus 100 is also provided herein. The method comprises disposing the thermal transfer apparatus 100 in a freezer to cool the thermal transfer apparatus 100 to a temperature of less than or equal to the second freezing point. The second thermal transfer media can freeze and the first thermal transfer media may not freeze depending on the first freezing point and the temperature of the freezer. The thermal transfer apparatus 100 can be removed from the freezer and disposed against a portion of a body of a patient and conformed to the portion of the body of the patient so that the thermal transfer apparatus 100 can absorb heat from the portion of the body of the patient. Heat can be absorbed through the first wall 104 and/or the second wall 106 by the transfer of kinetic energy from particle to particle. When heat is absorbed by the first thermal transfer media, the first thermal transfer media may have a non-uniform temperature (e.g., first thermal transfer media closer to the first wall 104 and/or second wall 106 may be warmer than first thermal transfer media further away from the first wall 104 and/or the second wall 106. If the first thermal transfer media has a varying temperature, the density also varies causing circulation and movement of liquid portions of the first thermal transfer media. The warmed first thermal transfer media can pass by and contact the third wall 118 and/or 120 and heat can be absorbed there through into the second thermal transfer media.

Figure 3:
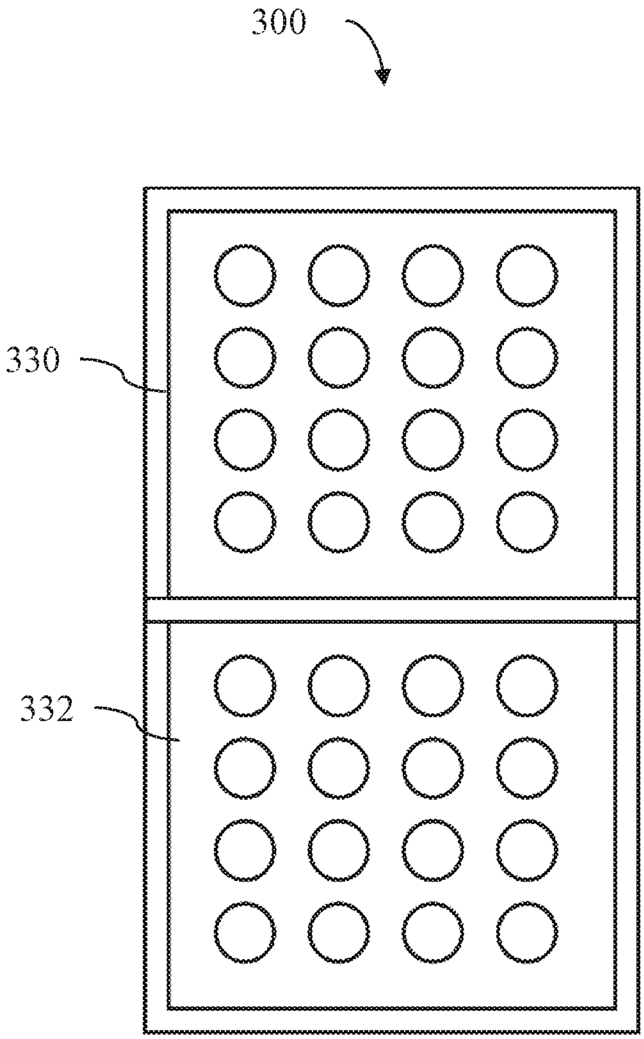
FIG. 3 is top view illustrating an example of a thermal transfer apparatus comprising two modules according to the present disclosure.
Figure 17:
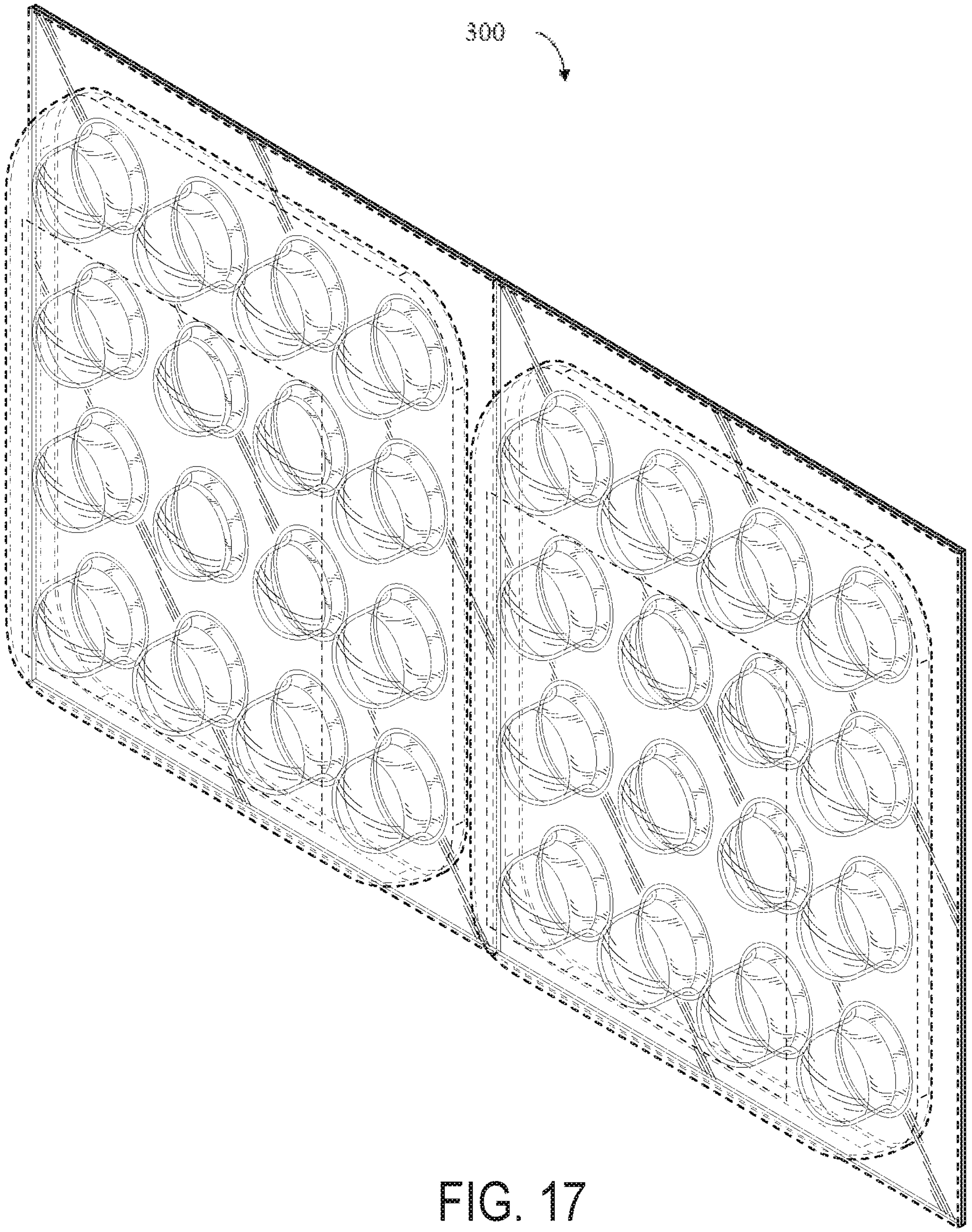
FIG. 17 is a front perspective view of an example of a thermal transfer apparatus comprising two modules according to the present disclosure.
Figure 18:
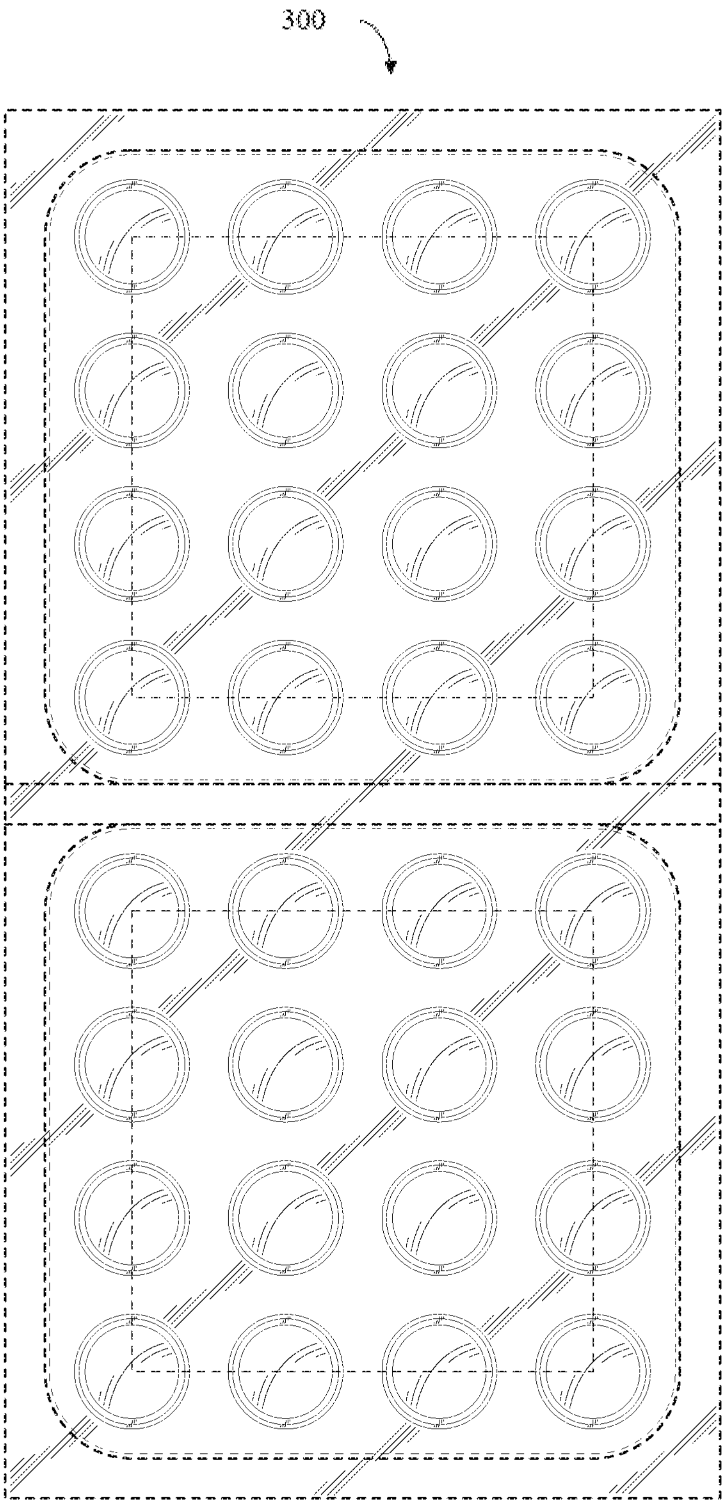
FIG. 18 is a top view of the thermal transfer apparatus of FIG. 17 shown in a first configuration of use.
Figure 19:
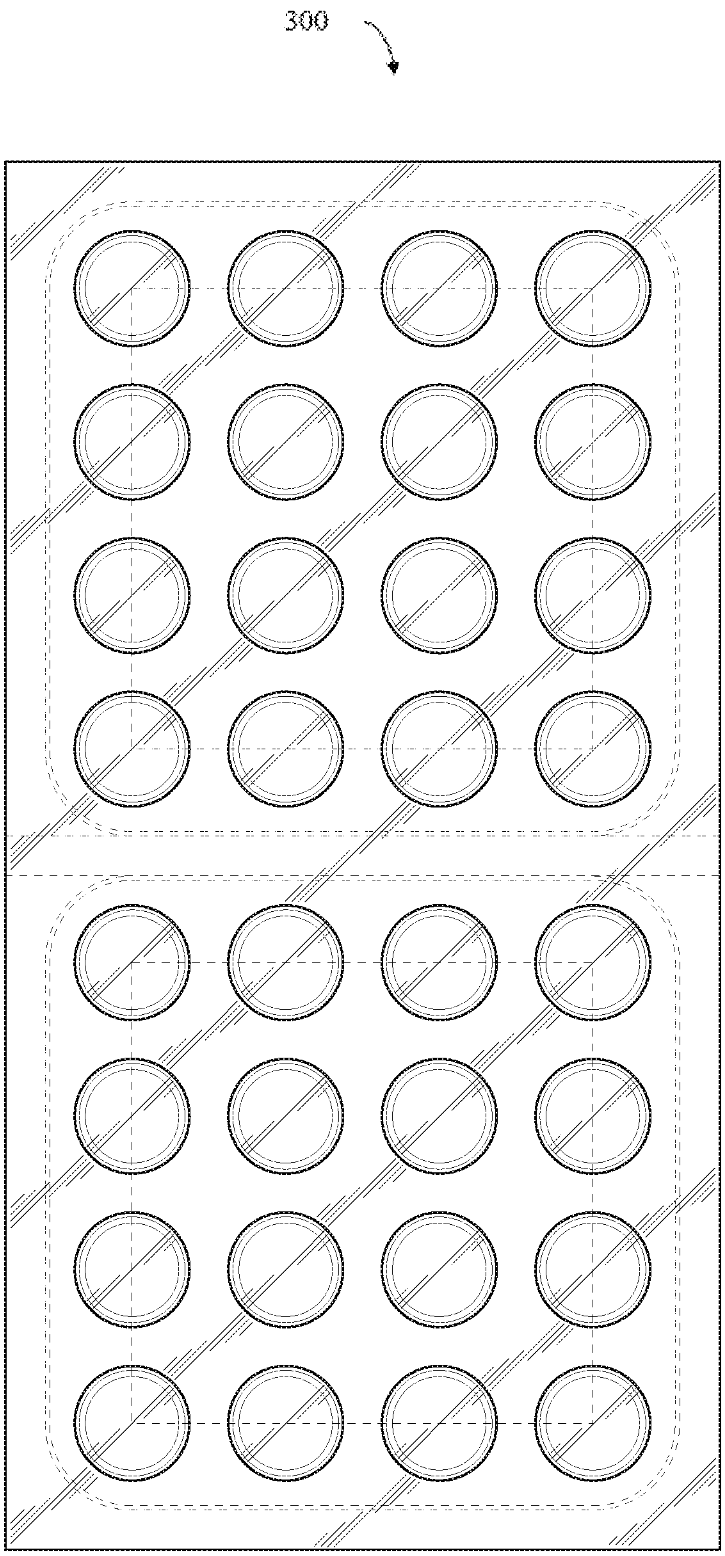
FIG. 19 is a bottom view of the thermal transfer apparatus of FIG. 17.

The thermal transfer apparatus can comprise at least two modules. For example, referring to FIG. 3, a thermal transfer apparatus 300 is provided with two modules 330 and 332. Each module 330 and 332 can be the same or different. For example, the modules 330 and 332 can be configured the same as the thermal transfer apparatus 100. The modules are connected together at edges 104*a* and 106*a*. In various examples, the first walls 104 of modules 330 and 332 can be part of a single continuous piece through all modules 330 and 332 and the second walls 106 of modules 330 and 332 can be part of a single continuous piece through all modules 330 and 332. The edges 104*a* and 106*a* can be portions of the thermal transfer apparatus 300 that are fused together by, for example, a heat sealing or other adhesive technique such that the first wall 104 is fused to the second wall 106. An example of the thermal transfer apparatus 300 is shown in FIGS. 17-19.

Figure 4:
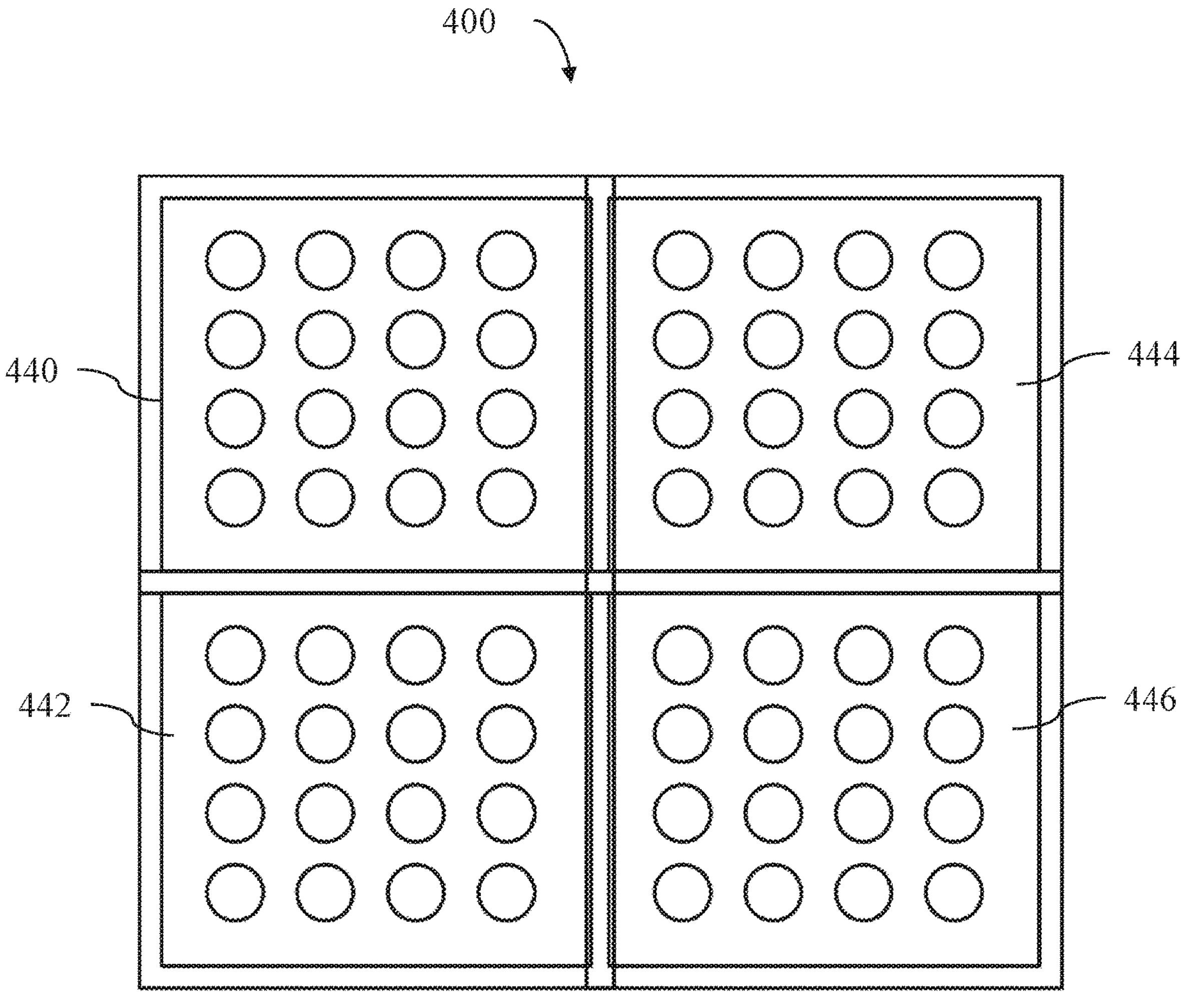
FIG. 4 is top view illustrating an example of a thermal transfer apparatus comprising four modules according to the present disclosure.
Figure 20:
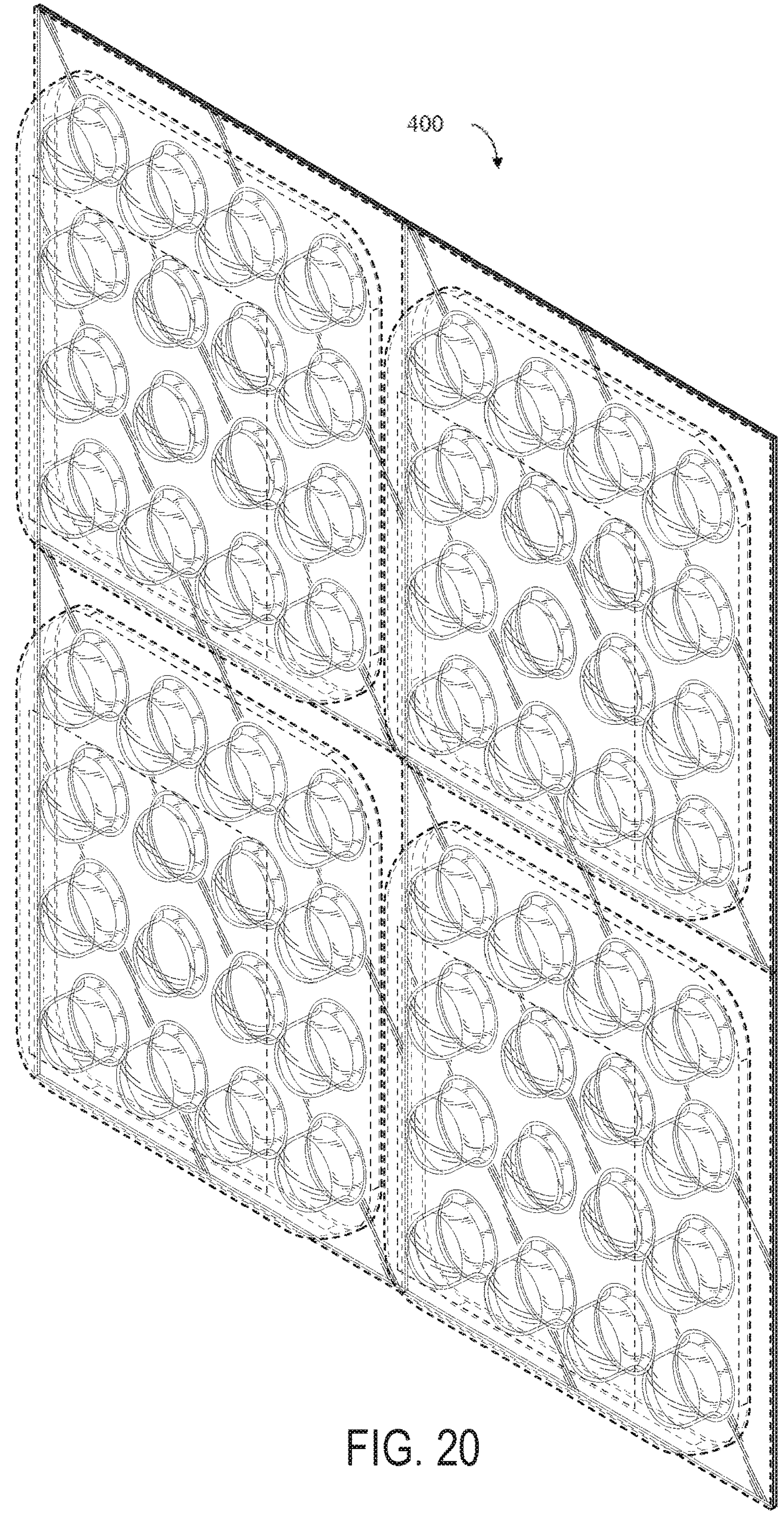
FIG. 20 is a front perspective view illustrating an example of a thermal transfer apparatus comprising four modules according to the present disclosure.
Figure 21:
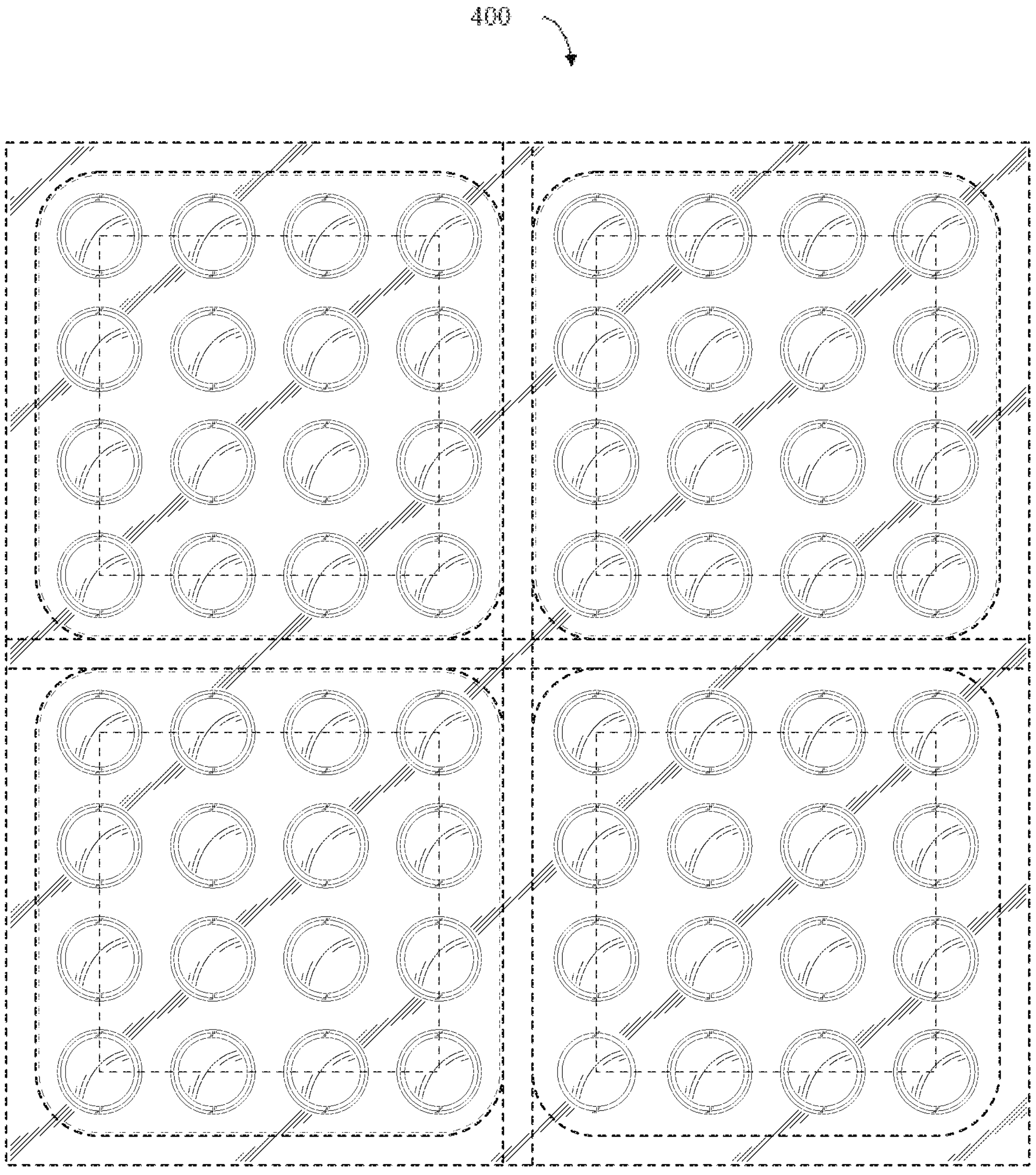
FIG. 21 is a top view of the thermal transfer apparatus of FIG. 20.
Figure 22:
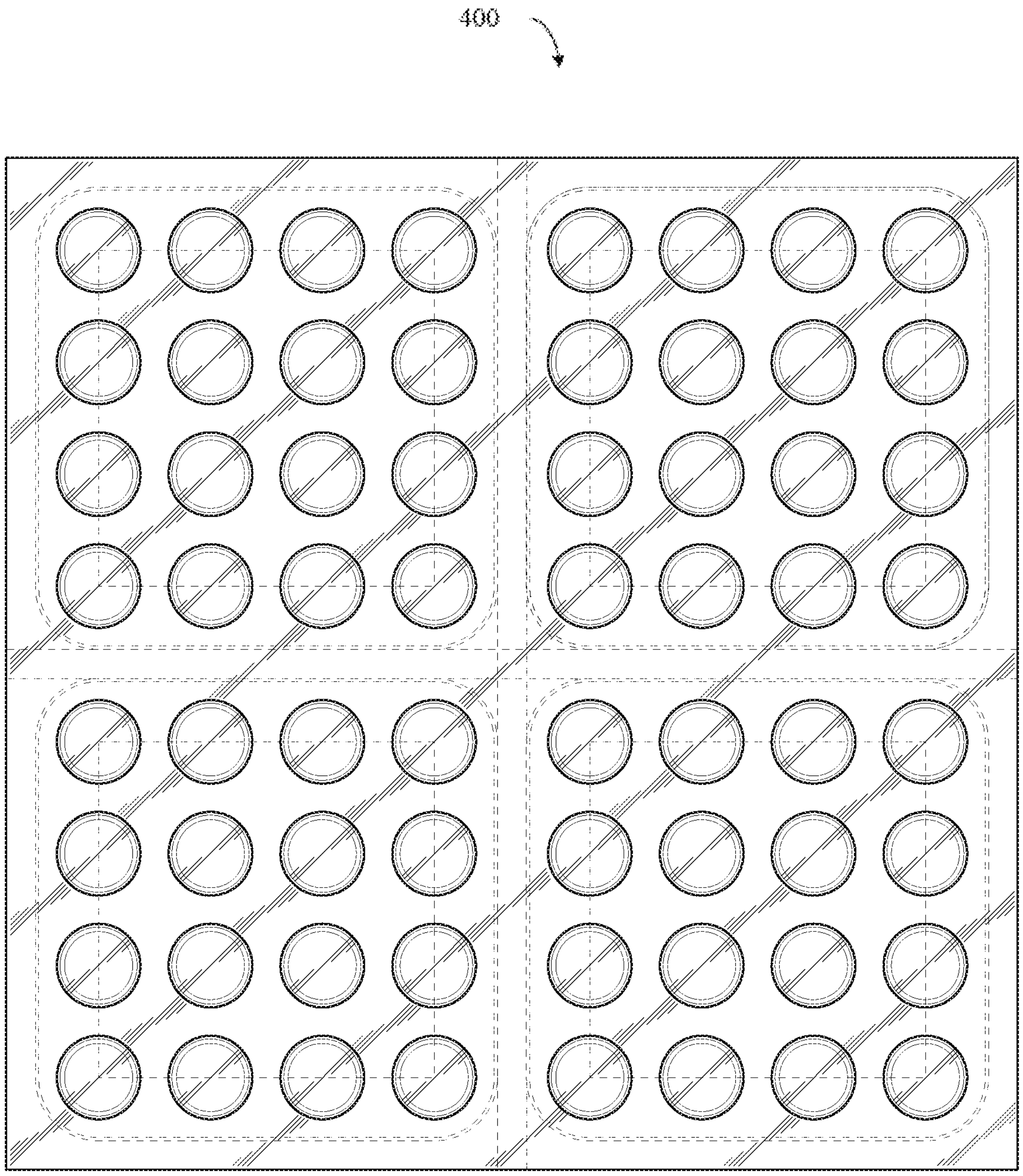
FIG. 22 is a bottom view of the thermal transfer apparatus of FIG. 20.

Referring to FIG. 4, a thermal transfer apparatus 400 is provided with four modules 440, 442, 444, and 446 in a first configuration. Each module 440, 442, 444, and 446 can be the same or different. For example, the modules 440, 442, 444, and 446 can be configured the same as the thermal transfer apparatus 100. The modules 440, 442, 444, and 446 are connected together at edges 104*a* and 106*a*. In various examples, the first walls 104 of modules 440, 442, 444, and 446 can be part of a single continuous piece through all modules 440, 442, 444, and 446 and the second walls 106 of modules 440, 442, 444, and 446 can be part of a single continuous piece through all modules 440, 442, 444, and 446. The edges 104*a* and 106*a* can be portions of the thermal transfer apparatus 300 that are fused together by, for example, a heat sealer such that the first wall 104 is fused to the second wall 106. An example of the thermal transfer apparatus 400 is shown in FIGS. 20-22.

Figure 5:
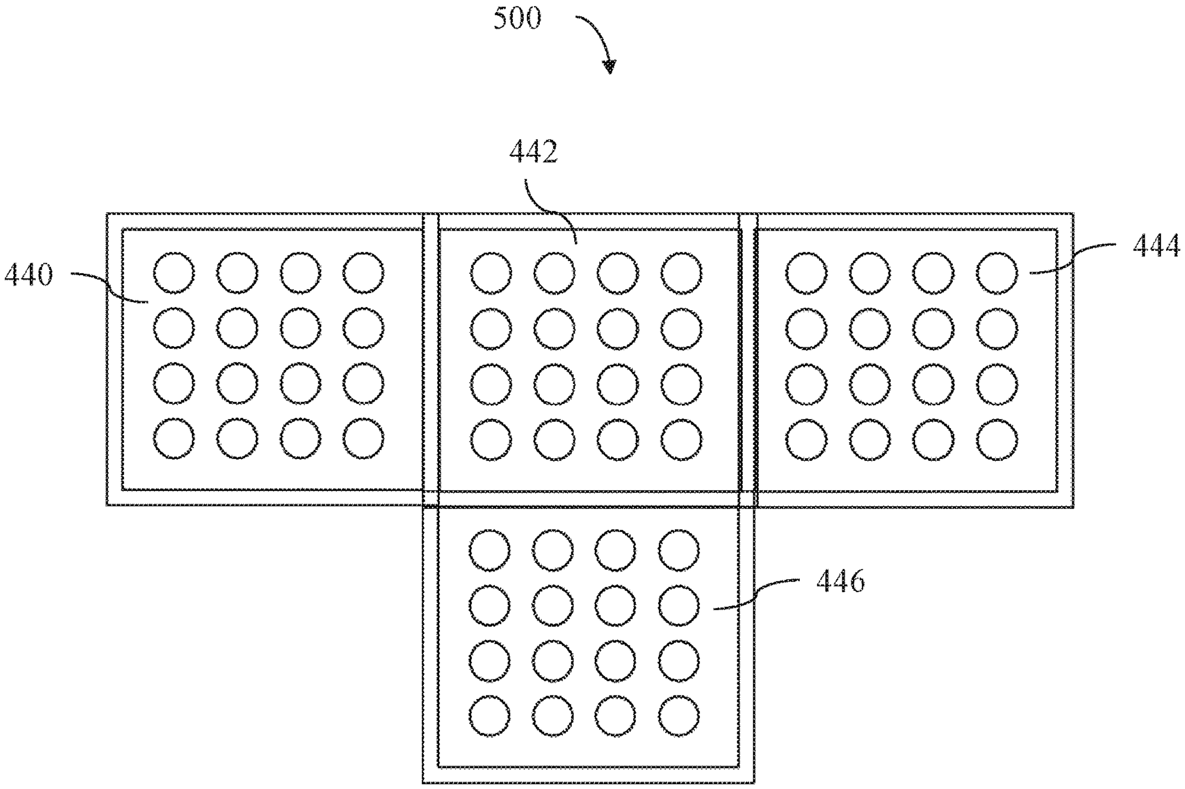
FIG. 5 is top view illustrating an example of a thermal transfer apparatus comprising four modules configured in a T-shape according to the present disclosure.
Figure 6:
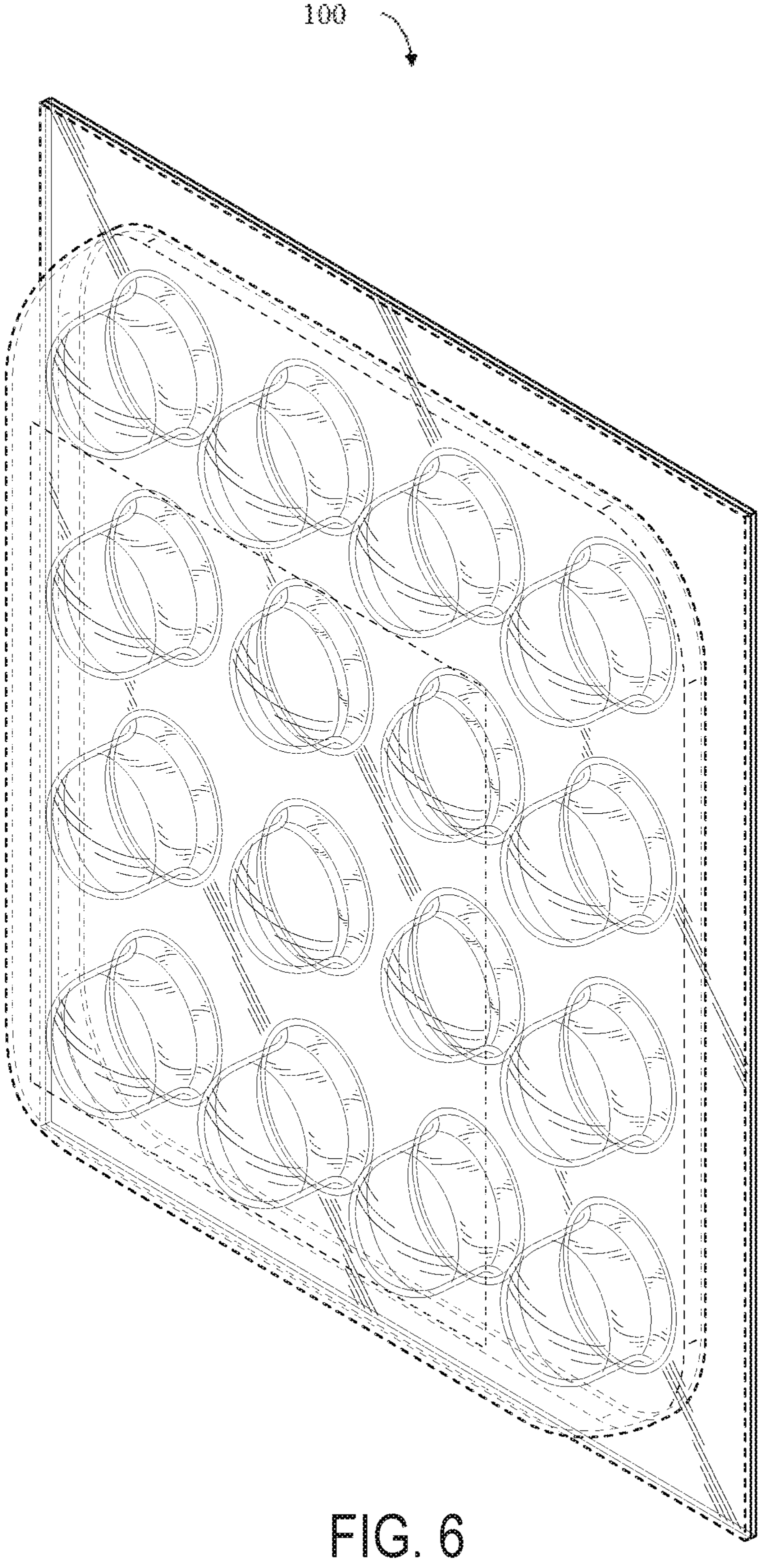
FIG. 6 is a front perspective view illustrating an example of a thermal transfer apparatus according to the present disclosure.
Figure 7:
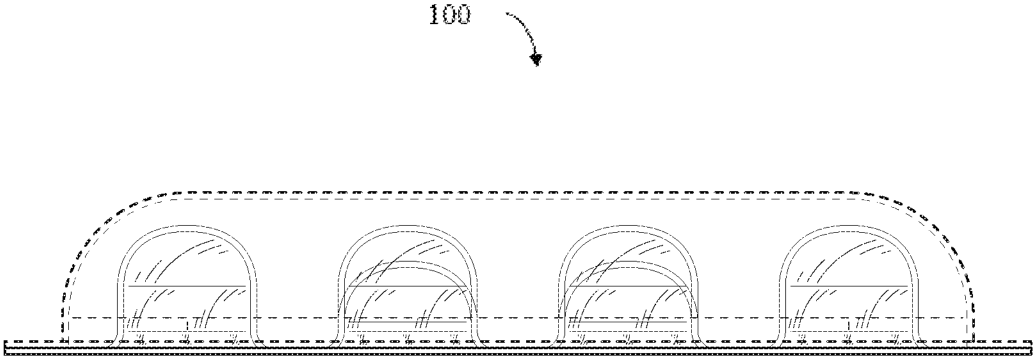
FIG. 7 is a front elevational view of the thermal transfer apparatus of FIG. 6.
Figure 8:
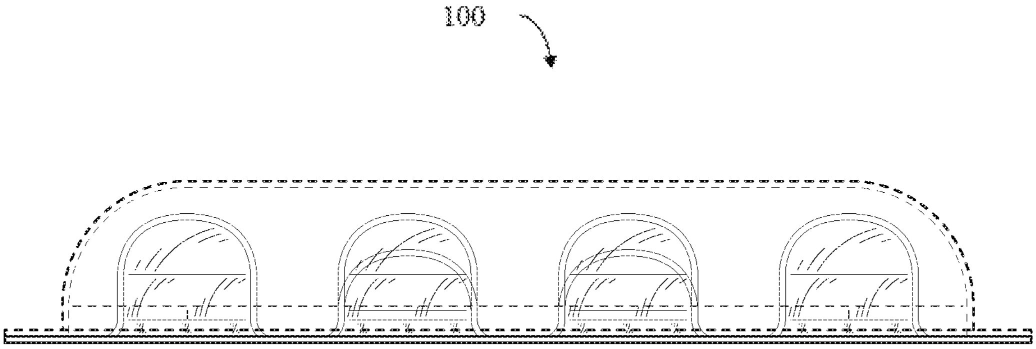
FIG. 8 is a left side elevational view of the thermal transfer apparatus of FIG. 6.
Figure 9:
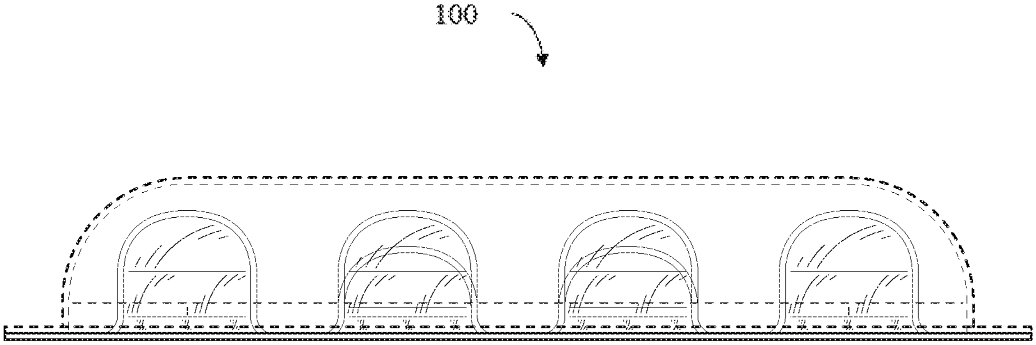
FIG. 9 is a right side elevational view of the thermal transfer apparatus of FIG. 6.
Figure 10:
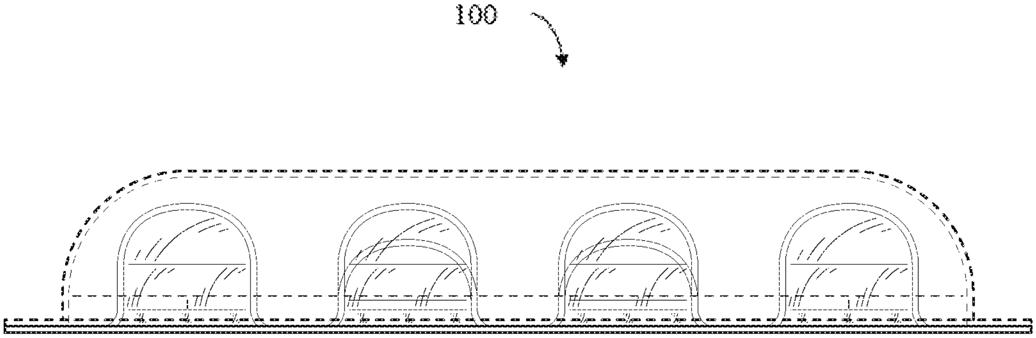
FIG. 10 is a rear elevational view of the thermal transfer apparatus of FIG. 6.
Figure 11:
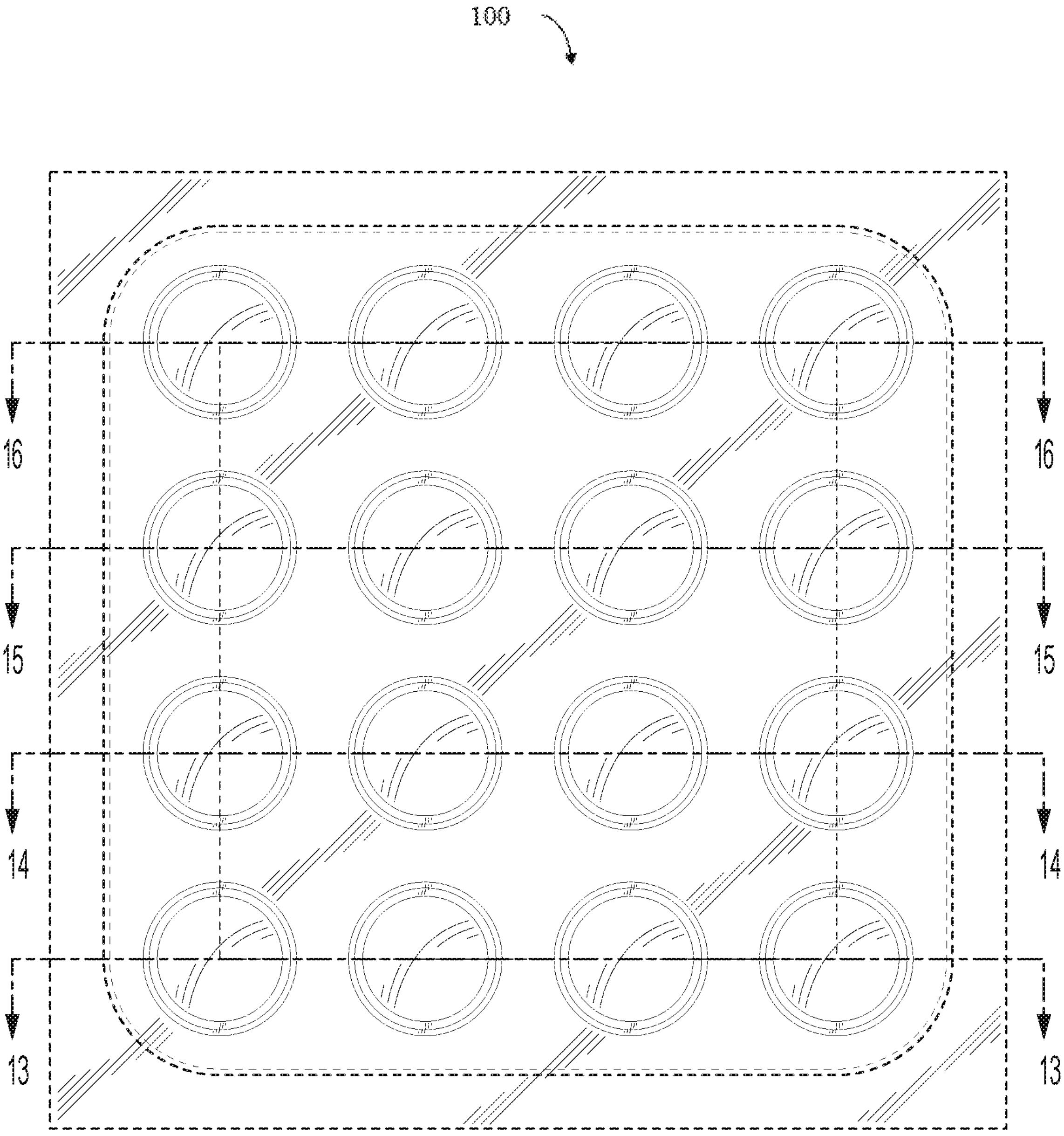
FIG. 11 is a top view of the thermal transfer apparatus of FIG. 6.
Figure 12:
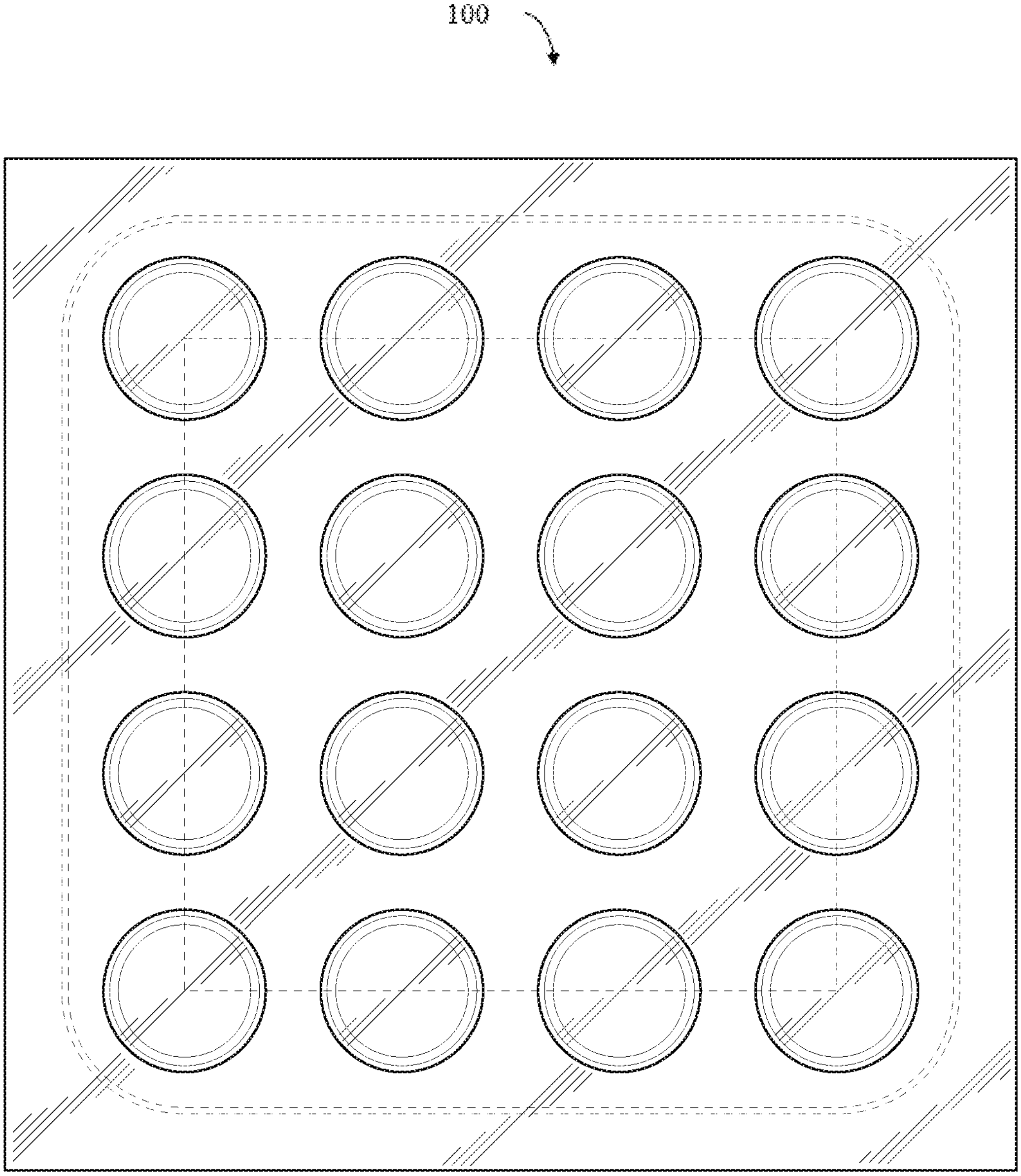
FIG. 12 is a bottom view of the thermal transfer apparatus of FIG. 6.
Figure 13:
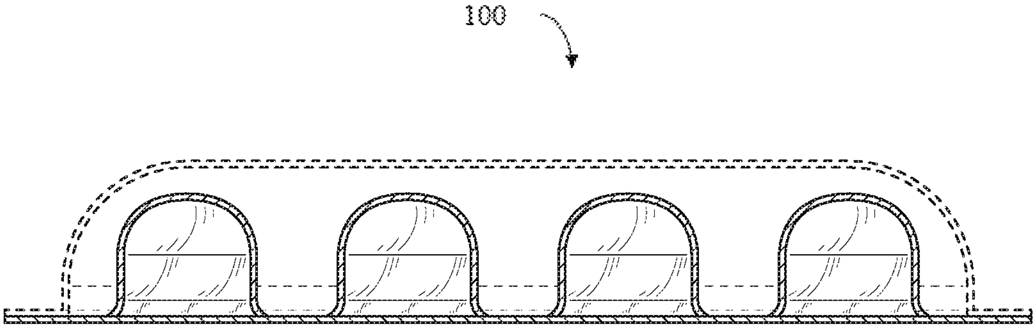
FIG. 13 is a cross-sectional view of the thermal transfer apparatus of FIG. 6, sectioned along line 13-13 in FIG. 11.
Figure 14:
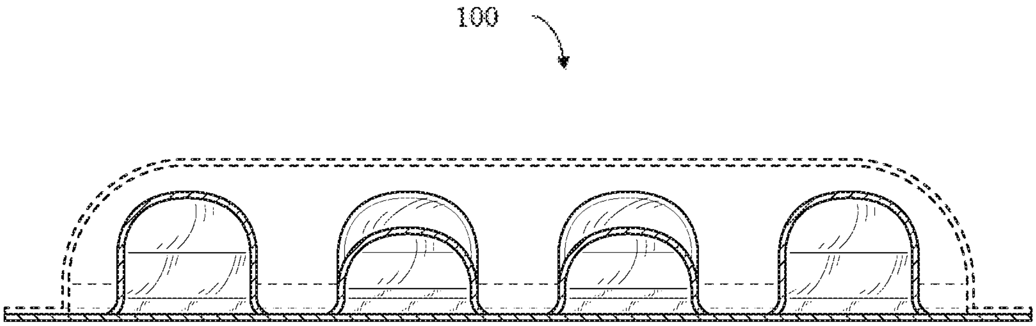
FIG. 14 is a cross-sectional view of the thermal transfer apparatus of FIG. 6, sectioned along line 14-14 in FIG. 11.
Figure 15:
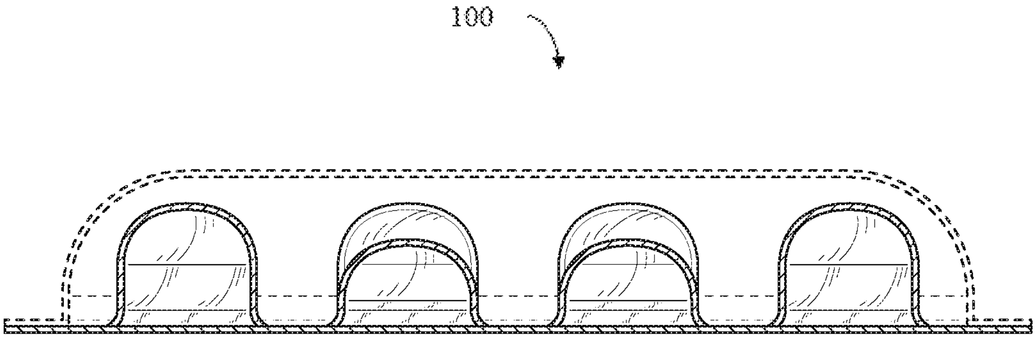
FIG. 15 is a cross-sectional view of the thermal transfer apparatus of FIG. 6, sectioned along line 15-15 in FIG. 11.
Figure 16:
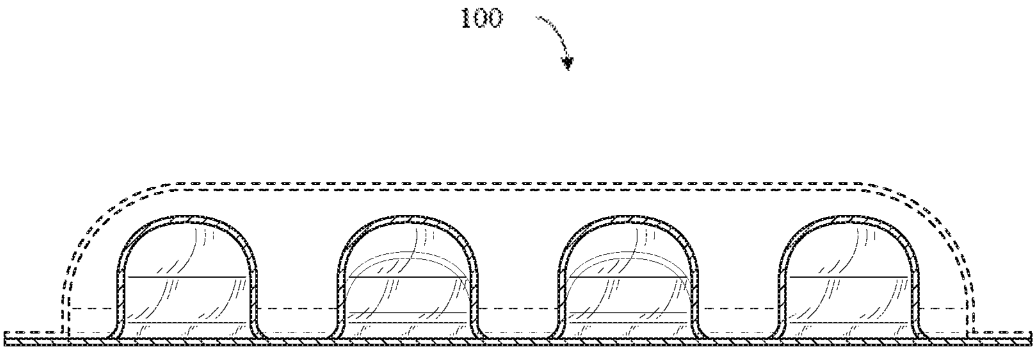
FIG. 16 is a cross-sectional view of the thermal transfer apparatus of FIG. 6, sectioned along line 16-16 in FIG. 11.
Figure 23:
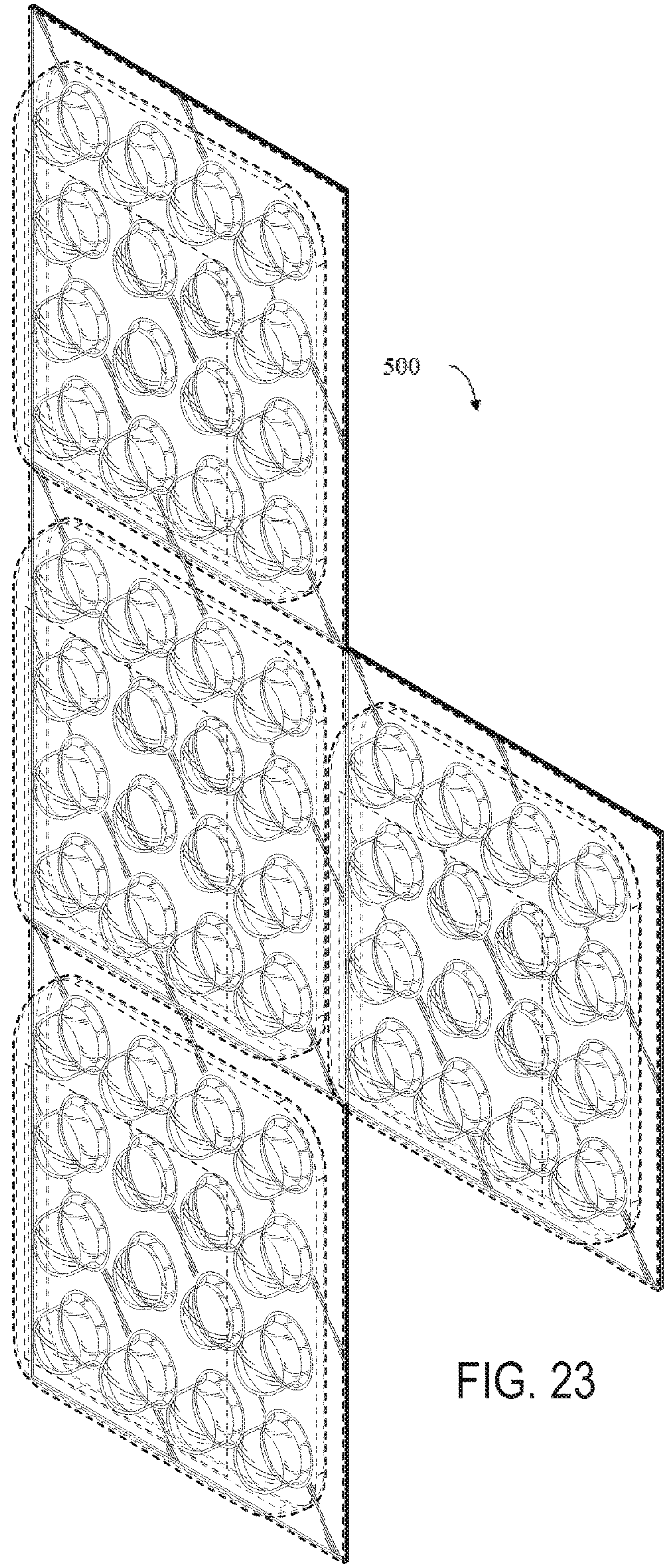
FIG. 23 is a front perspective view illustrating an example of a thermal transfer apparatus comprising four modules configured in a T-shape according to the present disclosure.
Figure 24:
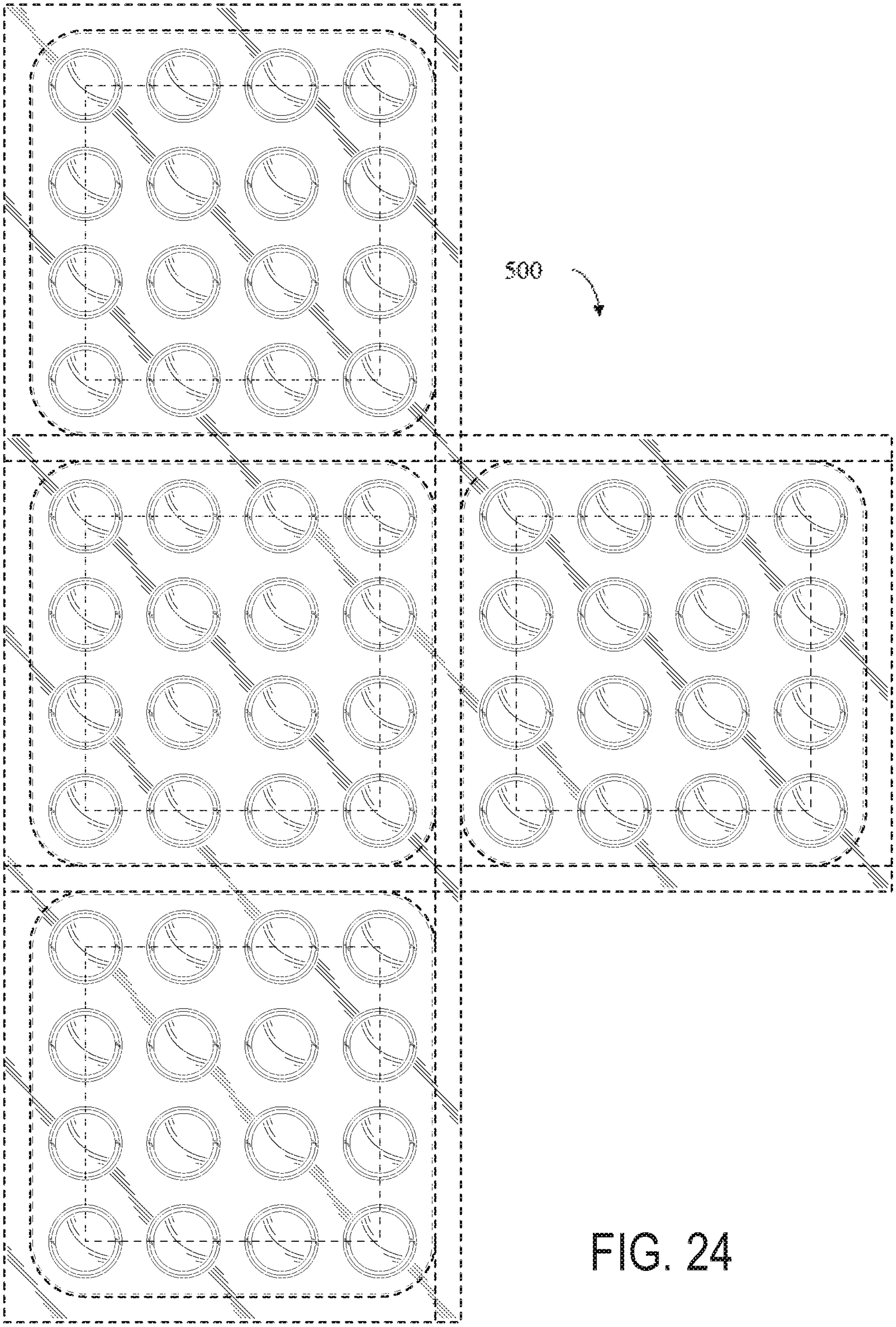
FIG. 24 is a top view of the thermal transfer apparatus of FIG. 23.
Figure 25:
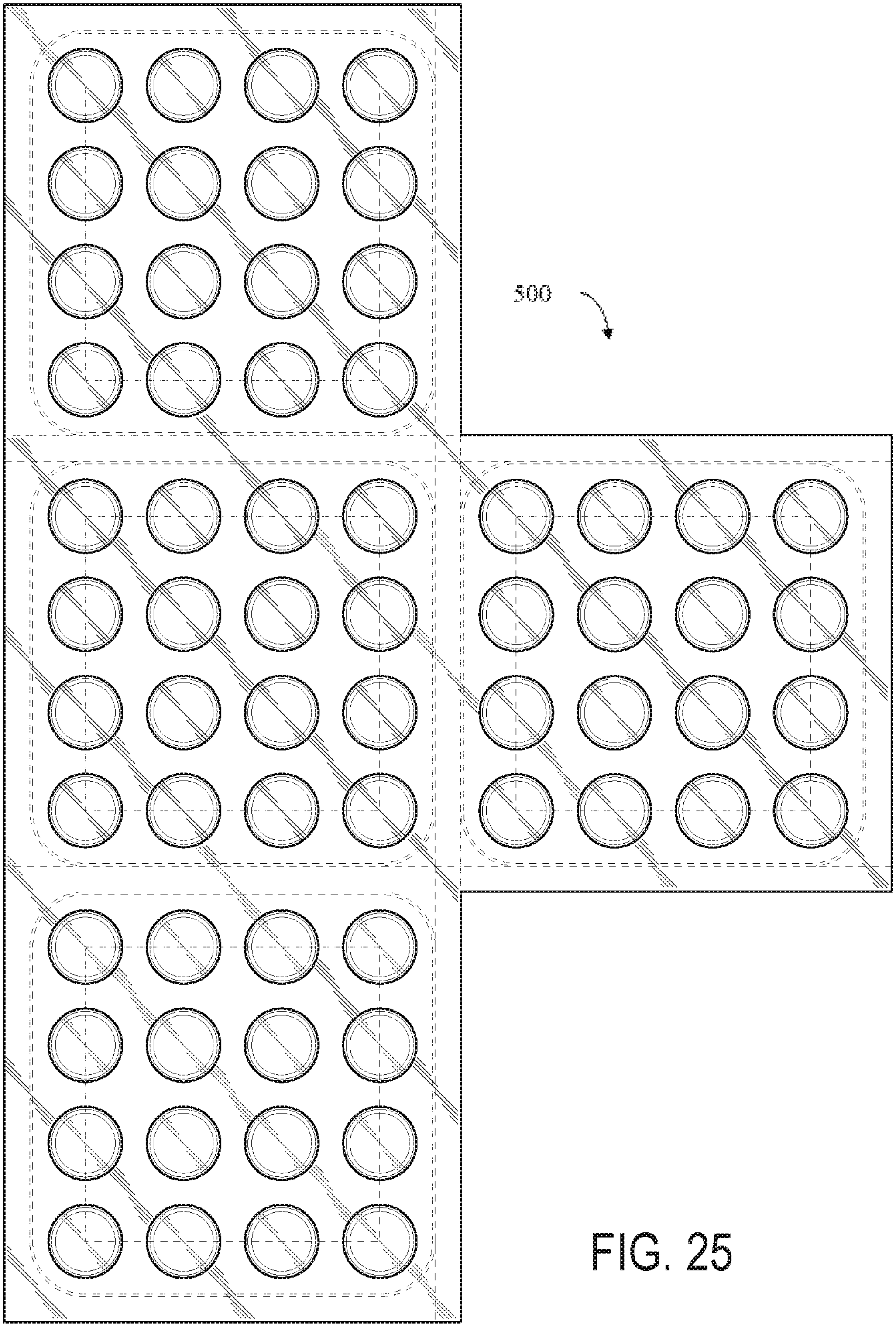
FIG. 25 is a bottom view of the thermal transfer apparatus of FIG. 23.

Referring to FIG. 5, a thermal transfer apparatus 500 is provided with modules 440, 442, 444, and 446 in a second configuration, such as, for example, a T-shape. An example of the thermal transfer apparatus 500 is shown in FIGS. 23-25.

The following numbered clauses are directed to various non-limiting embodiments and aspects according to the present disclosure.

Clause 1. A thermal transfer apparatus comprising: a first container comprising a first wall, and a second wall connected to the first wall at ends of each wall, thereby defining a first enclosed cavity, at least four protrusions extending from the first wall into the first enclosed cavity towards the second wall and each protrusion comprising a third wall defining a second enclosed cavity, wherein the at least four protrusions comprise at least two short protrusions and at least two long protrusions, the short protrusions extend a first distance from the first wall into the first enclosed cavity towards the second wall, and are positioned intermediate two or more of the long protrusions, and the long protrusions extend a second distance from the first wall into the first enclosed cavity towards the second wall, the second distance is greater than the first distance; a first thermal transfer media positioned within the first enclosed cavity; and a second thermal transfer media positioned within each second enclosed cavity, wherein the first thermal transfer media has a first freezing point lower than a second freezing point of the second thermal transfer media.

Clause 2. The thermal transfer apparatus of clause 1, wherein the at least four protrusions are arranged in a grid.

Clause 3. The thermal transfer apparatus of any of clauses 1-2, further comprising sixteen protrusions including the at least four protrusions, wherein the sixteen protrusions are arranged in four rows and four columns to form a first module.

Clause 4. The thermal transfer apparatus of clause 3, further comprising at least two modules, including the first module, coupled together.

Clause 5. The thermal transfer apparatus of any of clauses 1-4, wherein each protrusion tapers away from the first wall.

Clause 6. The thermal transfer apparatus of any of clauses 1-5, wherein each protrusion comprises a rounded cross-section in a plane parallel to the first wall.

Clause 7. The thermal transfer apparatus of any of clauses 1-6, wherein the first distance is in a range of 0.25 inches to 1.25 inches.

Clause 8. The thermal transfer apparatus of any of clauses 1-7, wherein the second distance is in a range of 0.75 inches to 1.5 inches.

Clause 9. The thermal transfer apparatus of any of clauses 1-8, wherein a third distance between each protrusion is in a range of 0.1 inches to 1.25 inches.

Clause 10. The thermal transfer apparatus of any of clauses 1-9, wherein the second distance is greater than the first distance by at least 0.05 inches.

Clause 11. The thermal transfer apparatus of any of clauses 1-10, wherein the second distance is greater than the first distance by at least 0.1 inches.

Clause 12. The thermal transfer apparatus of any of clauses 1-11, wherein the first freezing point is lower than the second freezing point by at least 3 degrees Celsius.

Clause 13. The thermal transfer apparatus of any of clauses 1-12, wherein the first freezing point is lower than the second freezing point by at least 5 degrees Celsius.

Clause 14. The thermal transfer apparatus of any of clauses 1-13, wherein the second freezing point is in a range of −5 degrees Celsius to 5 degrees Celsius.

Clause 15. The thermal transfer apparatus of any of clauses 1-14, wherein the first thermal transfer media and the second thermal transfer media, individually, comprises water, glycol, gelatin, a hydrogel, or a combination thereof.

Clause 16. The thermal transfer apparatus of clause 15, wherein the first thermal transfer media and the second thermal transfer media, individually, further comprise chitosan.

Clause 17. The thermal transfer apparatus of any of clauses 1-16, wherein the first wall, the second wall, and the third wall, each comprise plastic.

Clause 18. The thermal transfer apparatus of any of clauses 1-17, wherein the first wall, the second wall, and the third wall, each comprise a thickness in a range of 0.5 mm to 5 mm.

Clause 19. A method comprising disposing the thermal transfer apparatus of any of clauses 1-18 in a freezer to cool the thermal transfer apparatus to a temperature of less than or equal to the second freezing point, thereby forming a cool thermal transfer apparatus; and disposing the cooled thermal transfer apparatus against a portion of a body of a patient and conforming the cooled thermal transfer apparatus against the portion of the body of the patient to absorb heat.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

The grammatical articles "a", "an", and "the", as used herein, are intended to include "at least one" or "one or more", unless otherwise indicated, even if "at least one" or "one or more" is expressly used in certain instances. Thus, the foregoing grammatical articles are used herein to refer to one or more than one (i.e., to "at least one") of the particular identified elements. Further, the use of a singular noun includes the plural, and the use of a plural noun includes the singular, unless the context of the usage requires otherwise.

As used herein, "intermediate" means that the referenced element is disposed between two elements but is not necessarily in contact with those elements. Accordingly, unless stated otherwise herein, an element that is "intermediate" a first element and a second element may or may not be adjacent to or in contact with the first and/or second elements, and other elements may be disposed between the intermediate element and the first and/or second elements.

One skilled in the art will recognize that the herein described thermal support, structures, operations/actions, and objects, and the discussion accompanying them, are used as examples for the sake of conceptual clarity and that various configuration modifications are contemplated. Consequently, as used herein, the specific examples/embodiments set forth and the accompanying discussion are intended to be representative of their more general classes. In general, use of any specific exemplar is intended to be representative of its class, and the non-inclusion of specific components, devices, apparatus, operations/actions, and objects should not be taken as limiting. While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed and not as more narrowly defined by particular illustrative aspects provided herein.

What is claimed is:

1. A thermal transfer apparatus comprising:

a first container comprising a first wall, and a second wall connected to the first wall at ends of each wall, thereby defining a first enclosed cavity, at least four protrusions extending from the first wall into the first enclosed cavity towards the second wall and each protrusion comprising a third wall defining a second enclosed cavity, wherein the at least four protrusions comprise at least two short protrusions and at least two long protrusions, the short protrusions extend a first distance from the first wall into the first enclosed cavity towards the second wall, and are positioned intermediate two or more of the long protrusions, the long protrusions extend a second distance from the first wall into the first enclosed cavity towards the second wall, the second distance is greater than the first distance, and the long protrusions extend along a perimeter of the thermal transfer apparatus and the short protrusions are in an interior of the thermal transfer apparatus;

a first thermal transfer media positioned within the first enclosed cavity; and a second thermal transfer media positioned within each second enclosed cavity, wherein the first thermal transfer media has a first freezing point lower than a second freezing point of the second thermal transfer media.

2. The thermal transfer apparatus of claim 1, wherein the at least four protrusions are arranged in a grid.

3. The thermal transfer apparatus of claim 1, further comprising sixteen protrusions including the at least four protrusions, wherein the sixteen protrusions are arranged in four rows and four columns to form a first module.

4. The thermal transfer apparatus of claim 3, further comprising at least two modules, including the first module, coupled together.

5. The thermal transfer apparatus of claim 1, wherein each protrusion tapers away from the first wall.

6. The thermal transfer apparatus of claim 1, wherein each protrusion comprises a rounded cross-section in a plane parallel to the first wall.

7. The thermal transfer apparatus of claim 1, wherein the first distance is in a range of 0.25 inches to 1.25 inches.

8. The thermal transfer apparatus of claim 1, wherein the second distance is in a range of 0.75 inches to 1.5 inches.

9. The thermal transfer apparatus of claim 1, wherein a third distance between each protrusion is in a range of 0.1 inches to 1.25 inches.

10. The thermal transfer apparatus of claim 1, wherein the second distance is greater than the first distance by at least 0.05 inches.

11. The thermal transfer apparatus of claim 1, wherein the second distance is greater than the first distance by at least 0.1 inches.

12. The thermal transfer apparatus of claim 1, wherein the first freezing point is lower than the second freezing point by at least 3 degrees Celsius.

13. The thermal transfer apparatus of claim 1, wherein the first freezing point is lower than the second freezing point by at least 5 degrees Celsius.

14. The thermal transfer apparatus of claim 1, wherein the second freezing point is in a range of −5 degrees Celsius to 5 degrees Celsius.

15. The thermal transfer apparatus of claim 1, wherein the first thermal transfer media and the second thermal transfer media, individually, comprises water, glycol, gelatin, a hydrogel, or a combination thereof.

16. The thermal transfer apparatus of claim 15, wherein the first thermal transfer media and the second thermal transfer media, individually, further comprise chitosan.

17. The thermal transfer apparatus of claim 1, wherein the first wall, the second wall, and the third wall, each comprise plastic.

18. The thermal transfer apparatus of claim 1, wherein the first wall, the second wall, and the third wall, each comprise a thickness in a range of 0.5 mm to 5 mm.

19. A method comprising:

disposing the thermal transfer apparatus of claim 1 in a freezer to cool the thermal transfer apparatus to a temperature of less than or equal to the second freezing point, thereby forming a cool thermal transfer apparatus; and disposing the cooled thermal transfer apparatus against a portion of a body of a patient and conforming the cooled thermal transfer apparatus against the portion of the body of the patient to absorb heat.

* * * * *